(12) United States Patent
Bellani et al.

(10) Patent No.: US 6,407,252 B1
(45) Date of Patent: Jun. 18, 2002

(54) PROCESS FOR THE SYNTHESIS OF RITONAVIR

(75) Inventors: Pietro Bellani, Rho; Marco Frigerio, Milan; Patrizia Castoldi, Lainate, all of (IT)

(73) Assignee: Clariant Life Science Molecules (Italy) S.p.A., Milan (IT)

( * ) Notice: Subject to any disclaimer, the term of this patent is extended or adjusted under 35 U.S.C. 154(b) by 0 days.

(21) Appl. No.: 09/856,455

(22) PCT Filed: Sep. 18, 2000

(86) PCT No.: PCT/IT00/00368
§ 371 (c)(1),
(2), (4) Date: May 21, 2001

(87) PCT Pub. No.: WO01/21603
PCT Pub. Date: Mar. 29, 2001

(30) Foreign Application Priority Data

Sep. 21, 1999 (IT) .......................................... MI99A1950

(51) Int. Cl.[7] ...................... C07D 277/22; C07D 277/28
(52) U.S. Cl. ........................................ 548/203; 548/205
(58) Field of Search .................................. 548/203, 205

(56) References Cited

U.S. PATENT DOCUMENTS

| | | | |
|---|---|---|---|
| 5,354,866 A | | 10/1994 | Kempf et al. |
| 5,491,253 A | | 2/1996 | Stuk et al. |
| 5,541,206 A | | 7/1996 | Kempf et al. |
| 5,559,158 A | * | 9/1996 | Al-Razzak et al. ......... 514/616 |
| 5,567,823 A | * | 10/1996 | Tien et al. .................. 548/204 |

FOREIGN PATENT DOCUMENTS

| | | |
|---|---|---|
| EP | 0 748 801 | 12/1996 |
| WO | WO 94/14436 | 7/1994 |
| WO | 9604232 * | 2/1996 |
| WO | WO 98/00393 | 1/1998 |
| WO | WO 98/54122 | 12/1998 |
| WO | WO 99/11636 | 3/1999 |

OTHER PUBLICATIONS

PCT Search Report
L. Cotarca et al., Bis(Trichloromethyl) Carbonate in Organic Synthesis, XP–002090854, pp. 553–576, 1996.

* cited by examiner

*Primary Examiner*—Floyd D. Higel
*Assistant Examiner*—Golam M. M. Shameem
(74) *Attorney, Agent, or Firm*—Scott E. Hanf

(57) ABSTRACT

A process is described which permits the preparation of Ritonavir with only five intermediate stages using the same starting materials as those used in the process described in WO 94/14436; the process described here is also particularly satisfactory from the point of view of environmental impact because nearly all of the carbon atoms used are subsequently incorporated in the final molecule. Finally, the improvement afforded by this novel process is linked with the fact that an inexpensive reagent, such as bis-trichloromethyl carbonate (BTC), is used in two of the five stages.

20 Claims, 1 Drawing Sheet

PROCESS FOR THE SYNTHESIS OF RITONAVIR

This application is a 371 of PCT/IT00/00368 Sep. 18, 2000.

BACKGROUND OF THE INVENTION

Ritonavir (CAS Number [155213-67-5]), the structural formula of which is given below,

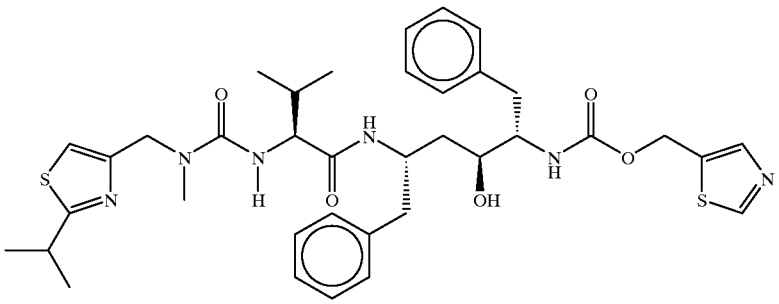

is an inhibitor of human HIV protease which was described for the first time by Abbott in International Patent Application WO 94/14436, together with the process for the preparation thereof.

In the synthesis scheme given in WO 94/14436, Ritonavir is manufactured starting from valine and from compounds 1, 4 and 7, the structural formulae of which are also given below.

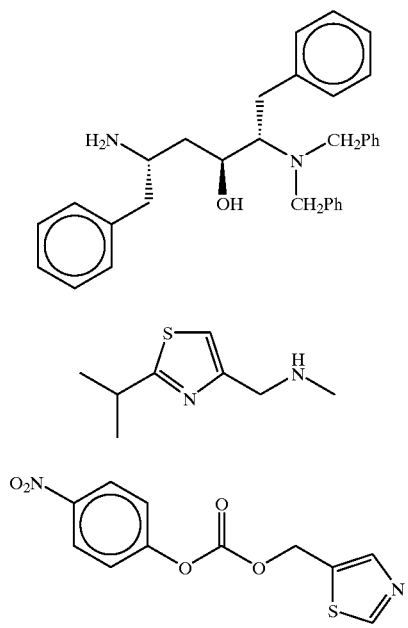

The synthesis process in question was subsequently optimised in its various parts by Abbot, who then described and claimed the individual improvements in the patent documents listed below: U.S. Pat. No. 5,354,866, U.S. Pat. No. 5,541,206, U.S. Pat. No. 5,491,253, WO 98/54122, WO 98/00393 and WO 99/11636.

The process for the synthesis of Ritonavir carried out on the basis of the abovementioned patent documents requires, however, a particularly large number of intermediate stages; it is also unacceptable from the point of view of so-called "low environmental impact chemical synthesis" (B. M. Trost Angew. Chem. Int. Ed. Engl. (1995) 34, 259–281) owing to the increased use of activating groups and protective groups which necessitate not inconsiderable additional work in disposing of the by-products of the process, with a consequent increase in the overall manufacturing costs.

SUMMARY OF THE INVENTION

The object of the present invention is therefore to find a process for the synthesis of Ritonavir which requires a smaller number of intermediate stages and satisfies the requirements of low environmental impact chemical synthesis, thus limiting "waste of material".

A process has now been found which, by using as starting materials the same compounds as those used in WO 94/14436, leads to the formation of Ritonavir in only five stages and with a minimum use of carbon atoms that are not incorporated in the final molecule.

DESCRIPTION OF THE DRAWING

The process, which constitutes the main subject of the present invention, is shown in FIG. 1.

DESCRIPTION OF THE PREFERRED EMBODIMENTS

Figure 1:
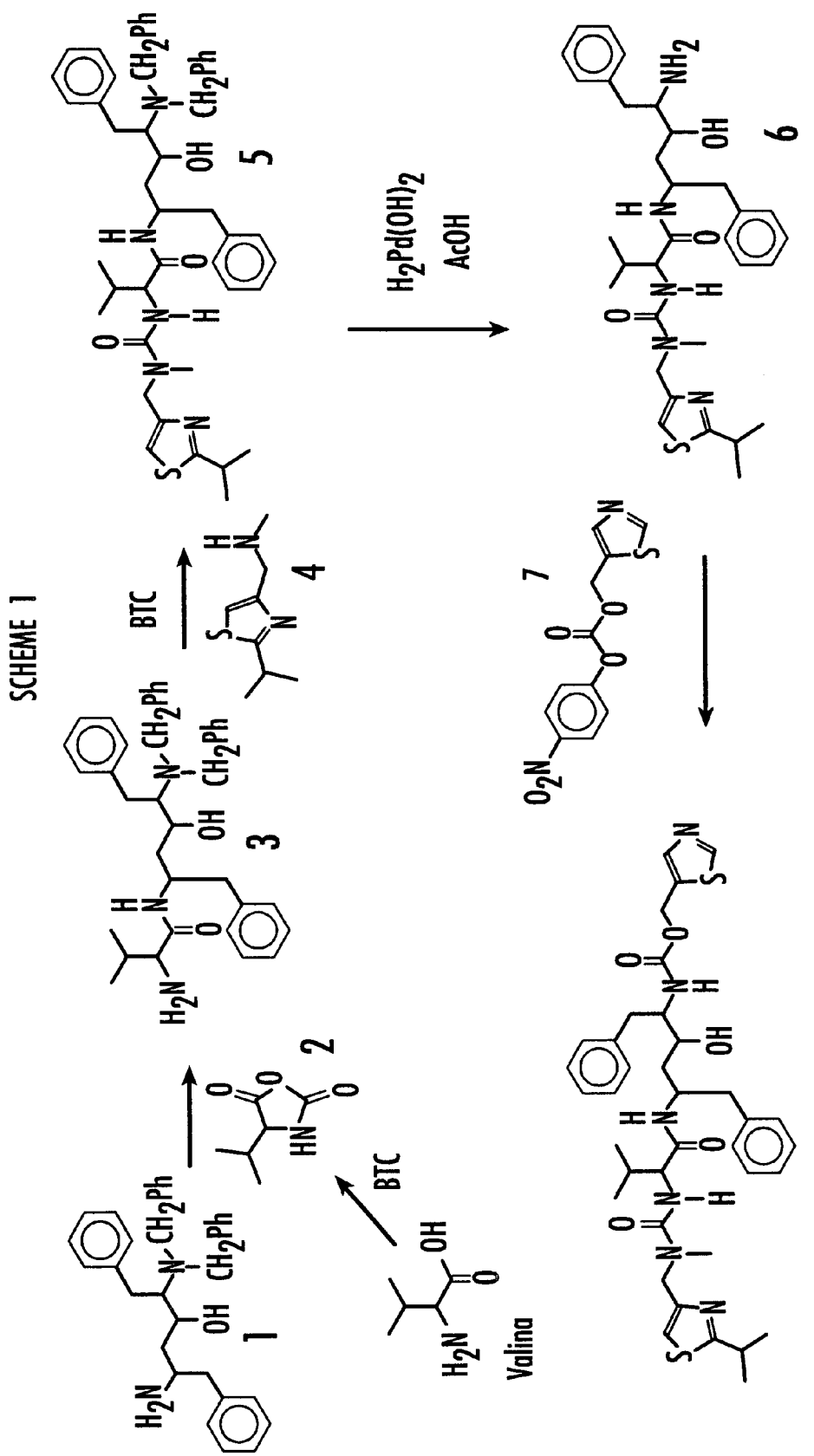

The process, which constitutes the main subject of the present invention is made up of the following stages:

(a) valine is condensed with bis-trichloromethyl carbonate to give intermediate 2, the structural formula of which is given below;

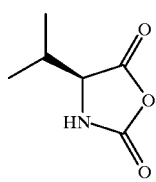

(b) intermediate 2 so obtained is reacted with compound 1 to give intermediate 3, the structural formula of which is given below;

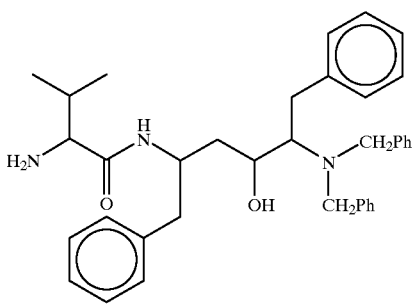

3

(c) intermediate 3 so obtained is reacted with compound 4 to give intermediate 5, the structural formula of which is given below;

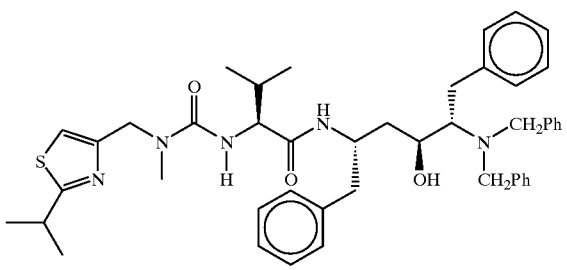

5

(d) the primary amine group of intermediate 5 is subjected to deprotection by removing the two benzyl groups to give intermediate 6, the structural formula of which is given below;

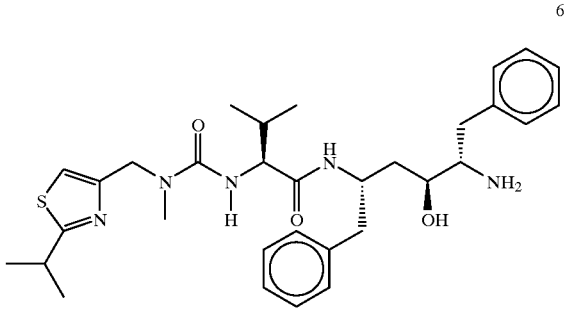

6

(e) intermediate 6 so obtained is reacted with compound 7 to give Ritonavir.

As any average person skilled in the art will appreciate, in addition to a reduced number of intermediate stages, the process according to the present invention also has a particular value from the point of view of environmental impact because, with the exception of a carbon atom used as an activator and protector of intermediate 5 and of the p-nitrophenol used as activator in the final reaction, all the carbon atoms used are then incorporated in the final molecule.

The improvement afforded by this new approach to synthesis is also linked with the fact that an inexpensive reagent, such as bis-trichloromethyl carbonate (BTC), is used in two of the total of five stages.

A second subject of the invention is represented by the compound of formula 3, which is novel per se, and by its use as an intermediate in the synthesis of Ritonavir. Finally, a further subject of the present invention is represented by the process for the preparation of the intermediate of formula 5.

From a practical point of view, stages (a) to (e) are carried out under standard reaction conditions which will be evident to any person skilled in the art; the preferred conditions of each individual stage are, however, listed hereinafter purely for purposes of illustration:

stage (a) is preferably carried out in an aprotic organic solvent, such as, for example, dioxane, tetrahydrofuran, $CH_2Cl_2$ and $CHCl_3$, at a temperature of from 20° C. to the reflux temperature of the solvent; dioxane is the preferred solvent.

stage (b) is preferably carried out in a non-polar organic solvent, even more preferably $CH_2Cl_2$, $CHCl_3$, $C_2H_2Cl_4$, in the presence of a tertiary amine, generally triethylamine, at a temperature of from −30 to 0° C.;

stage (c) is also preferably carried out in a non-polar organic solvent, such as $CH_2Cl_2$, $CHCl_3$, $C_2H_2Cl_4$, in the presence of a tertiary amine, generally triethylamine, at a temperature of from −20 to +10° C.;

the deprotection of the primary amine group of intermediate 5 (stage (d)) is preferably carried out by catalytic hydrogenation, generally on palladium; the solvent is preferably acetic acid, the temperature and the pressure are from +70 to +90° C. and from 3.5 to 5 bar, respectively;

stage (e) is preferably carried out in an aprotic polar organic solvent, even more preferably ethyl acetate, at a temperature of from +40 to +80° C.

Those and other aspects of the invention will become clear from the following Examples which are to be regarded as illustrative and non-limiting with respect to the invention.

EXAMPLES

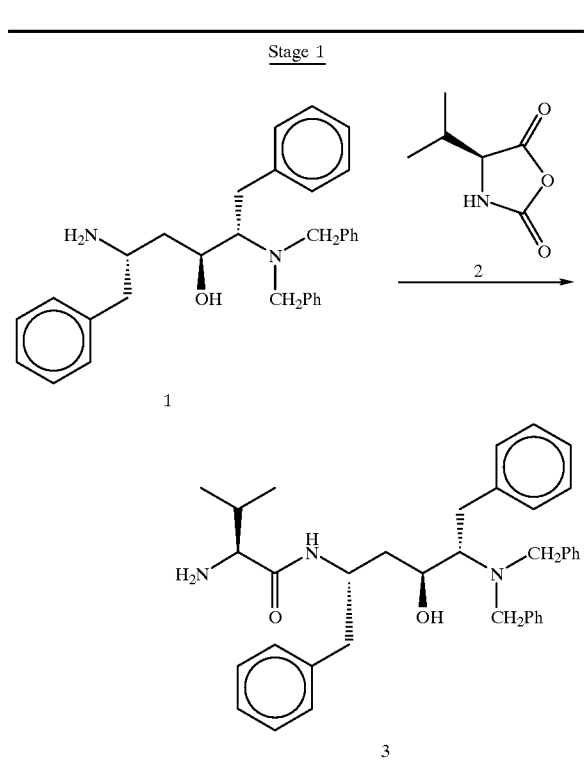

Stage 1

-continued

| Reagent | Molecular weight | Amount | Mmol | Eq. |
| --- | --- | --- | --- | --- |
| Amine 1 | 464.65 | 15 g | 32.282 | 1 |
| Val-NCA 2 | 142.13 | 6.9 g | 48.547 | 1.5 |
| Triethylamine | 101.19 (d = 0.726) | 4.5 ml | 32.283 | 1 |
| Dichloromethane | | 108 ml | | Sol. 0.3M |

Compound Val-NCA 2 was added to a solution of amine 1 (note 1, 2) in dichloromethane (60 ml) at −15° C. under nitrogen followed by a solution of triethylamine in dichloromethane (48 ml) (note 3). The reaction mixture was maintained under agitation at from −15° to −13° C. for two hours (note 4). The solution was used directly for the next stage without further purification.

Note 1. Amine 1 was prepared using the procedure described in A. R. Haight et al. Org. Proc. Res. Develop. (1999) 3, 94–100.

Note 2. Amine 1 was a mixture of stereoisomers with a ratio of 80:3.3:2.1:1.9.

Note 3. This solution was added dropwise over a period of 25 minutes.

Note 4. HPLC analysis after 2 hours: Amide 3 70.2%— starting material 4.3%

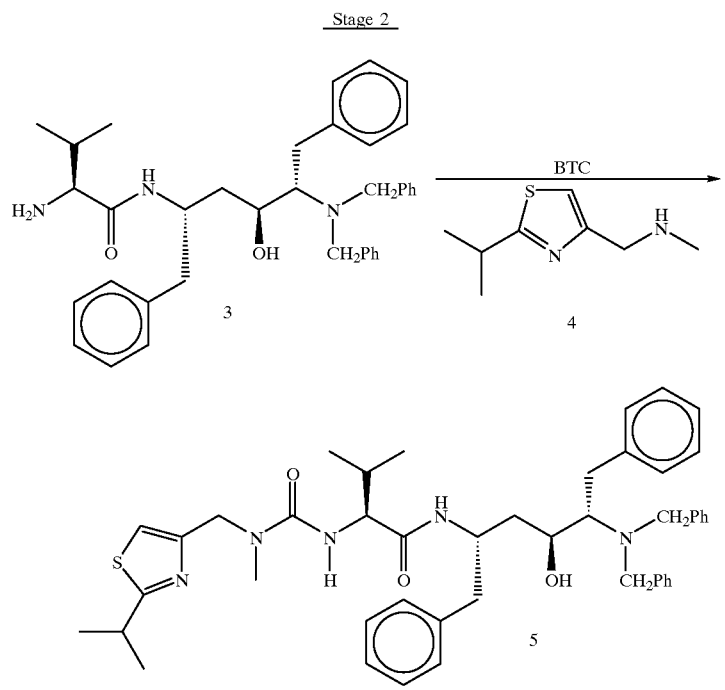

| Reagent | Molecular weight | Amount | Mmol | Eq. |
| --- | --- | --- | --- | --- |
| Amine 3 Solution from stage 1 | 563.78 | | 32.282 | 1 |
| Triethylamine | 101.19 (d = 0.726) | 2.6 ml | 18.654 | 0.6 |
| Bis(trichloromethyl)carbonate (BTC) | 296.75 | 3.5 g | 11.794 | 0.36 |
| Dichloromethane | | 65 ml | | |
| N-Methyl-4-aminomethyl-2-isopropylthiazole 4 | 170.27 | 5.5 g | 32.282 | 1 |
| Triethylamine | 101.19 (d = 0.726) | 6.9 ml | 49.504 | 1.5 |
| Dichloromethane | | 52 ml | | |

The triethylamine was added slowly to the solution of amine 3 resulting from stage 1 and this mixture was in turn added slowly to a solution of BTC in dichloromethane (65 ml) at from −15 to −13° C. and the reaction mixture was maintained under agitation at that temperature for 1.5 hours (note 1). A solution of amine 4 and triethylamine in dichloromethane (52 ml) was then added slowly to the reaction mixture (note 2) and maintained under agitation at that temperature for one hour (note 3). The reaction was stopped with water (97 ml) and the two phases were separated. The organic phase was 10 washed with a 10% aqueous citric acid solution, filtered over Celite and evaporated with a yield of 25 g of crude urea 5 which was purified by flash chroma tography on silica gel (eluant: toluene—ethyl acetate 6:4) to give 9.4 g of pure compound 5 (total yield of the two stages 38%) (note 4).

Note 1. HPLC analysis after 1.5 hours of the reaction stopped in tert-butylamine: Amide 3=0.41%—intermediate isocyanate=61.3%

Note 2. The solution of amine 4 was added over a period of approximately 20 minutes.

Note 3. HPLC analysis after 1 hour: Amide 3=7%—Urea 5=54%

Note 4. $^1$H-NMR(CDCl$_3$, 600 MHz) δ 7.31(m, 4H), 7.28–7.24(m, 4H), 7.21–7.14 (m, 8H), 7.11(d, 2H), 7.05(d, 2H), 6.96(s, 1H), 6.75(bd, 1H), 5.96(bs, 1H), 4.48(d, 1H), 4.39(d, 1H), 4.13(dd, 1H), 4.09(m, 1H), 3.93(bd, 2H), 3.56(bt, 1H), 3.39(d, 2H), 3.28(m, 1H), 3.04(dd, 1H), 2.97(s, 3H), 2.89(m, 1H), 2.74(q, 1H), 2.61(m, 2H), 2.25(m,1H), 1.53(ddd, 1H), 1.38(d, 6H), 1.28(dt, 1H), 0.98(d, 3H), 0.91(d, 3H).

reduced pressure. The crude product was dissolved in water (35 ml), the pH was adjusted to a value of 8 with NaOH, and extracted with CH$_2$Cl$_2$(2×15 ml). The organic phase was washed with water (10 ml) and the solvent was evaporated under reduced pressure with a yield of 1.8 g of amine 6 as a free base which was used for the next stage without further purification (note 3, 4).

Note 1. Of the various reaction conditions tested, such as HCOONH$_4$Pd—C in MeOH, H$_2$/Pd—C in methanol, H$_2$/Pd—C/CH$_3$SO$_3$H in methanol, H$_2$/Pd(OH)$_2$/C in methanol, etc., the best conditions we have found hitherto are those described in this Example.

Note 2. HPLC analysis after 5 hours: amine 6=52%—monobenzyl derivative=9.3%.

Note 3. HPLC analysis on the free base: amine 6=54%—monobenzyl derivative=6%.

Note 4. $^1$H-NMR (CDCl$_3$, 600 MHz) δ 7.29(m, 4H), 7.22–7.14(m, 6H), 7.00(s, 1H) 6.83(bd, 1H), 6.15(bs, 1H),

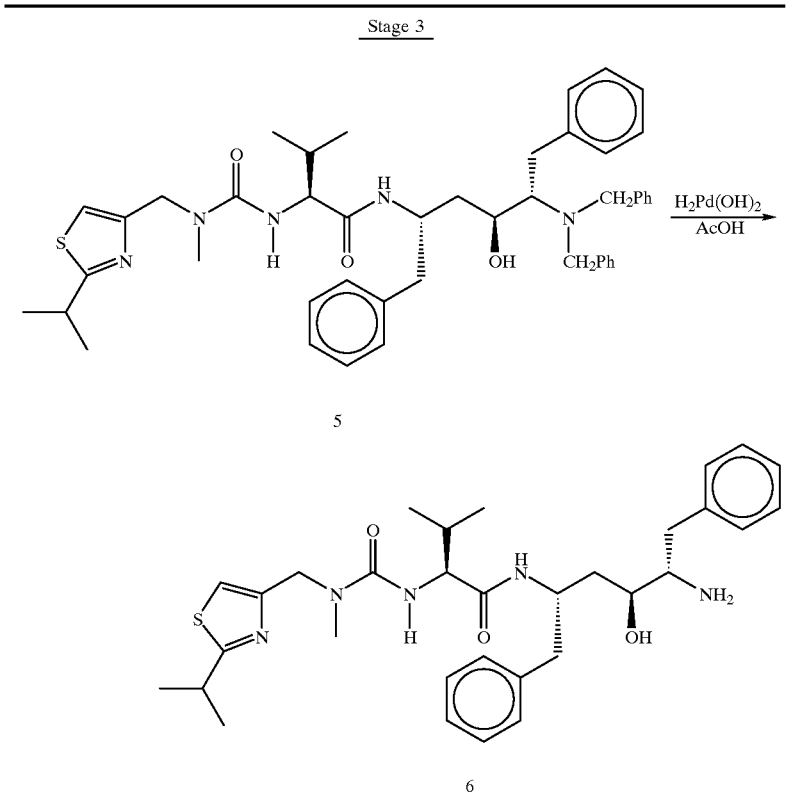

| Reagent | Molecular weight | Amount | Mmol | Eq. |
|---|---|---|---|---|
| Urea 5 | 760.05 | 3.5 g | 4.605 | 1 |
| Pd(OH)2/C 20% | | 5.25 g | | 30% w/w |
| Acetic acid | | 31 ml | | Sol. 0.15M |

The Pearlman catalyst (note 1) was added to a solution of urea 5 in acetic acid and the mixture was hydrogenated for 5 hours at from 4 to 4.5 bar and from 78 to 82° C. (note 2). The catalyst was filtered and the solvent was removed under 4.49(d, 1H), 4.41(d, 1H), 4.25(m, 1H), 4.08(m, 1H), 3.38(m, 1H), 3.29(m, 1H), 2.99(s, 3H), 2.92(dd 1H), 2.84(m, 2H), 2.76(m, 1H), 2.47(m, 1H), 2.28(m, 1H), 1.76(dt, 1H), 1.61 (dt, 1H), 1.38(d, 6H), 0.95(d, 3H), 0.89(d, 3H).

Stage 4

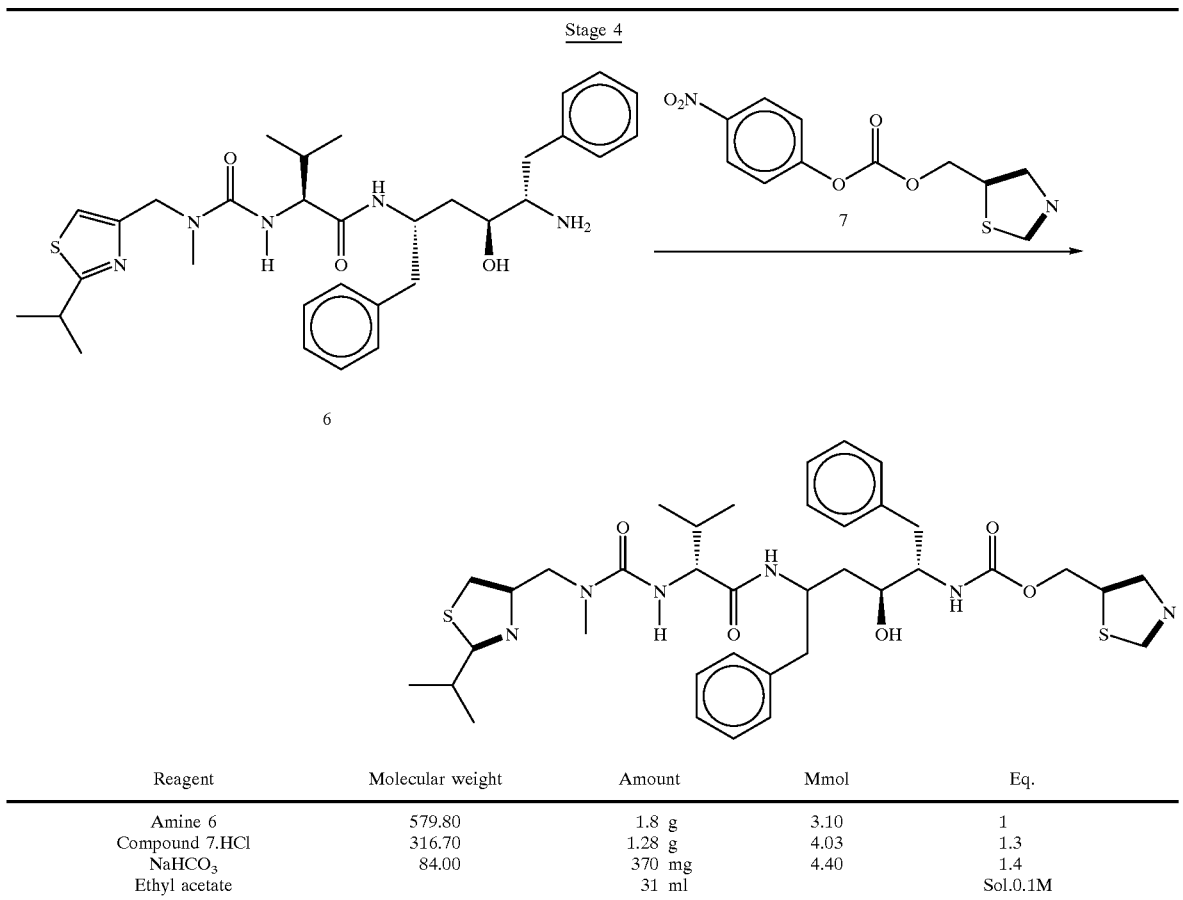

| Reagent | Molecular weight | Amount | Mmol | Eq. |
|---|---|---|---|---|
| Amine 6 | 579.80 | 1.8 g | 3.10 | 1 |
| Compound 7.HCl | 316.70 | 1.28 g | 4.03 | 1.3 |
| NaHCO$_3$ | 84.00 | 370 mg | 4.40 | 1.4 |
| Ethyl acetate | | 31 ml | | Sol.0.1M |

A solution of the chloride of compound 7 in ethyl acetate was treated with an aqueous sodium bicarbonate solution. The phases were separated and the organic phase was added to a solution of amine 6 in ethyl acetate. The reaction mixture was heated at 60° C. for 12 hours, then concentrated; ammonia was added and the solution was maintained under agitation for 1 hour. The organic phase was washed with a 10% aqueous potassium carbonate solution (3×5ml) and with a saturated sodium chloride solution (5 ml); the solvent was removed under reduced pressure. The crude product was purified by flash chromatography on silica gel (eluant ethyl acetate) to give 900 mg of pure Ritonavir (total yield of the two stages 27%) (note 1).

Note 1. $^1$H-NMR (DMSO, 600 MHz) δ 9.05(s, 1H), 7.86(s, 1H), 7.69(d, 1H), 7.22–7.10(m, 11H), 6.88(d, 1H), 6.02(d, 1H), 5.16(d, 1H), 5.12(d, 1H), 4.60(bs, 1H), 4.48(d, 1H), 4.42(d, 1H), 4.15(m, 1H), 3.94(dd, 1H), 3.83(m, 1H), 3.59(bt, 1H), 3.23(m, 1H), 2.87(s, 3H), 2.69–2.63(m, 3H), 2.60(m, 1H), 1.88(m, 1H), 1.45(m, 2H), 1.30(d, 6H), 0.74(d, 6H).

What is claimed is:

1. A process for the synthesis of Ritonavir, which comprises the following stages:

(a) valine is condensed with bis-trichloromethyl carbonate to give the compound

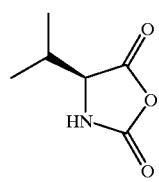

2

(b) that compound is reacted with compound

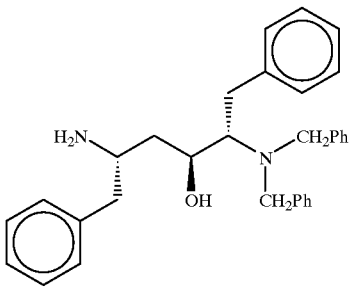

1 to give compound

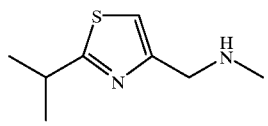

(c) that compound is reacted with compound

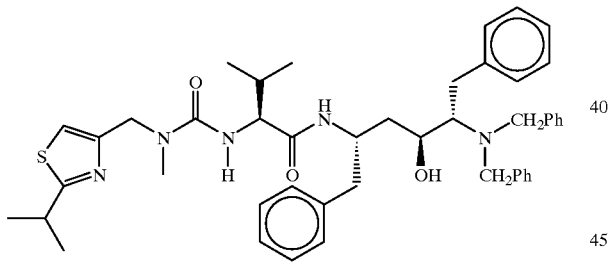

to give compound

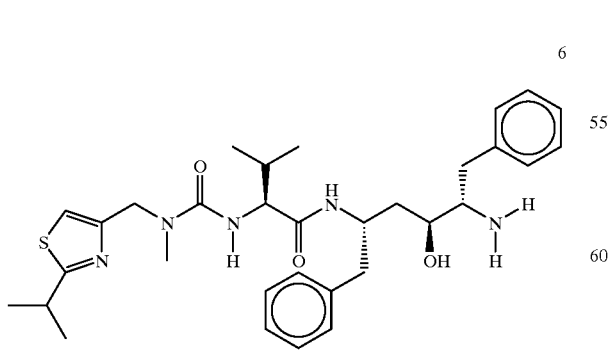

(d) the primary amine group of compound 5 is subjected to deprotection to give compound 6

(e) that compound is reacted with compound

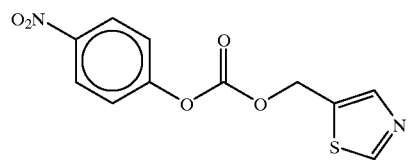

to give Ritonavir.

2. A process for the synthesis of the compound

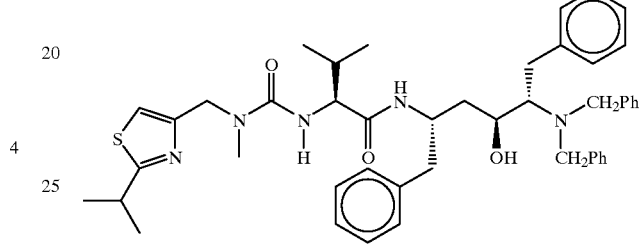

which comprises the following stages:

(a) valine is condensed with bis-trichloromethyl carbonate to give the compound

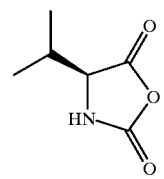

(b) that compound is reacted with compound

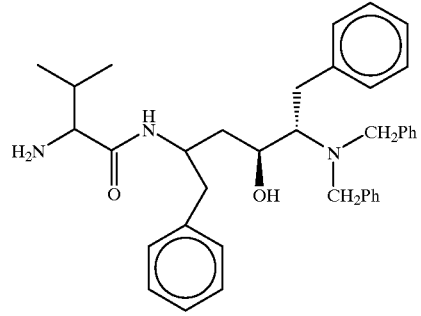

to give compound

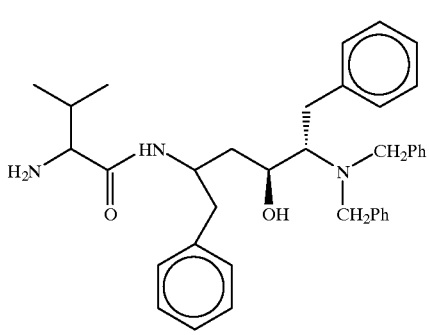

(c) that compound is reacted with compound

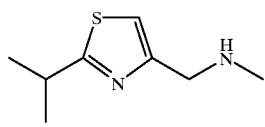

to give compound 5.

3. A process according to claim 1, wherein stage (a) is carried out in an aprotic organic solvent, such as, for example, dioxane, tetrahydrofuran, CH$_2$Cl$_2$ and CHCl$_3$, at a temperature of from 20° C. to the reflux temperature of the solvent.

4. A process according to claim 3, wherein the organic solvent is dioxane.

5. A process according to claim 1, wherein stage (b) is carried out in a non-polar organic solvent at a temperature of from −30 to 0° C.

6. A process according to claim 5, wherein the organic solvent is selected from CH$_2$Cl$_2$, CHCl$_3$, C$_2$H$_2$Cl$_4$.

7. A process according to claim 1, wherein stage (b) is carried out in the presence of a tertiary amine, preferably triethylamine.

8. A process according to claim 1, wherein stage (c) is carried out in a non-polar organic solvent at a temperature of from −20 to +10° C.

9. A process according to claim 8, wherein the organic solvent is selected from CH$_2$Cl$_2$, CHCl$_3$, C$_2$H$_2$Cl$_4$.

10. A process according to claim 1, wherein stage (c) is carried out in the presence of a tertiary amine, preferably triethylamine.

11. A process according to claim 1, wherein stage (d) is carried out by catalytic hydrogenation.

12. A process according to claim 11, wherein palladium is used as the catalyst.

13. A process according to claim 11, wherein the catalytic hydrogenation is carried out in acetic acid at a temperature of from +70 to +90° C. and at a pressure of from 3.5 to 5 bar.

14. A process according to claim 1, wherein stage (e) is carried out in an aprotic polar organic solvent, at a temperature of from +40 to +80° C.

15. A process according to claim 14, wherein the aprotic polar organic solvent is ethyl acetate.

16. A compound of formula

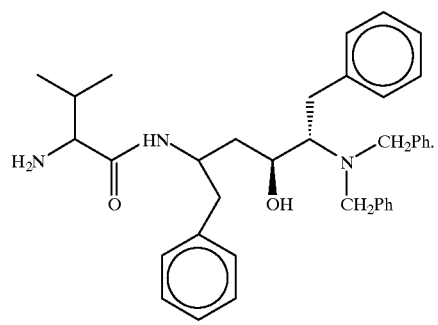

17. A method for the synthesis of Ritonavir comprising the steps of:

providing the compound of formula 3

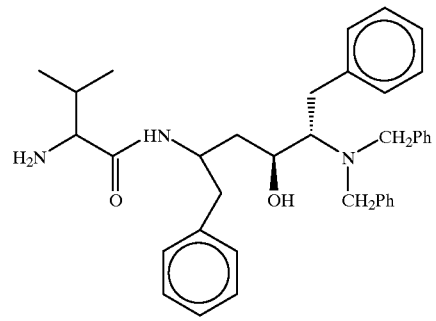

as claimed in claim 16;

reacting compound 3 with compound

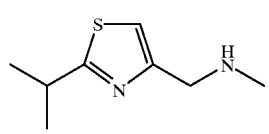

to give compound

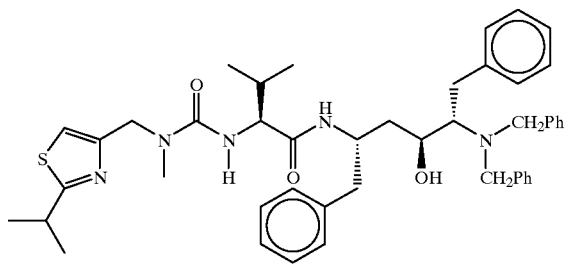

subjecting the primary amine group of compound 5 to deprotection to give compound reacting compound 6 with compound
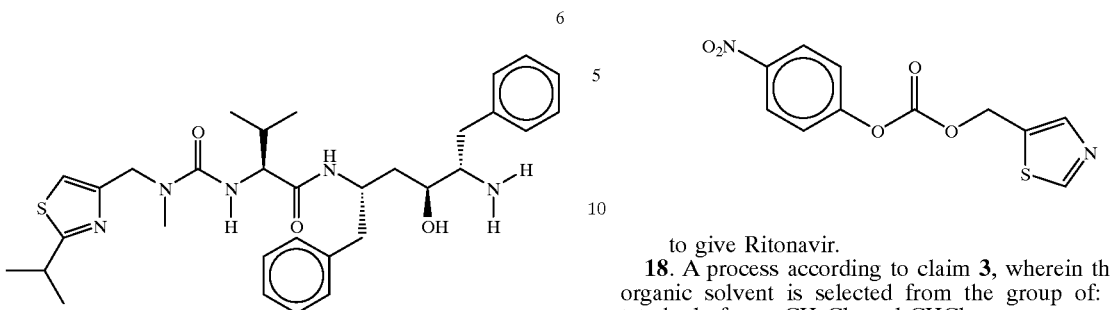
to give Ritonavir.
18. A process according to claim 3, wherein the aprotic organic solvent is selected from the group of: dioxane, tetrahydrofuran, CH$_2$Cl$_2$ and CHCl$_3$.
19. A process according to claim 7, wherein the tertiary arnine is triethylamine.
20. A process according to claim 10, wherein the tertiary amine is triethylamine.
* * * * *